United States Patent
Liu et al.

(10) Patent No.: US 12,054,759 B2
(45) Date of Patent: Aug. 6, 2024

(54) MUTANT-TYPE RNase R, AND PREPARATION METHOD THEREFOR AND APPLICATION THEREOF

(71) Applicant: Guangzhou Geneseed Biotech Co., Ltd., Guangzhou (CN)

(72) Inventors: Ming Liu, Guangzhou (CN); Qiujie Cai, Guangzhou (CN); Wanjun Zhang, Guangzhou (CN); MaoLei Zhang, Guangzhou (CN)

(73) Assignee: Guangzhou Geneseed Biotech Co., Ltd., Guangzhou (CN)

( * ) Notice: Subject to any disclaimer, the term of this patent is extended or adjusted under 35 U.S.C. 154(b) by 0 days.

(21) Appl. No.: 18/434,158

(22) Filed: Feb. 6, 2024

(65) Prior Publication Data

US 2024/0229004 A1 Jul. 11, 2024

Related U.S. Application Data

(63) Continuation of application No. PCT/CN2022/144252, filed on Dec. 30, 2022.

(30) Foreign Application Priority Data

Jan. 28, 2022 (CN) .......................... 2022101087308

(51) Int. Cl.
  *C12N 9/22* (2006.01)
  *C12N 9/88* (2006.01)
  *C12Q 1/6806* (2018.01)

(52) U.S. Cl.
  CPC ............. *C12N 9/88* (2013.01); *C12Q 1/6806* (2013.01); *C12Y 406/01* (2013.01)

(58) Field of Classification Search
  CPC ............ C12N 9/22; C12N 15/70; C12P 19/34
  See application file for complete search history.

(56) References Cited

FOREIGN PATENT DOCUMENTS

| CN | 108884450 A | 11/2018 |
|---|---|---|
| CN | 110923217 A | 3/2020 |
| CN | 115806970 A | 3/2023 |

*Primary Examiner* — Tekchand Saidha
(74) *Attorney, Agent, or Firm* — Nitin Kaushik

(57) ABSTRACT

The present invention relates to the technical field of molecular biology, and in particular, to a mutant-type RNase R and a preparation method therefor and application thereof. The mutant-type RNase R provided by the present invention is designated RNase R_ΔM8, an amino acid sequence of which is shown as SEQ ID NO. 5, and a nucleotide sequence encoding the amino acid sequence is shown as SEQ ID NO. 6. Preparation processes of the mutant-type RNase R_ΔM8 provided by the present invention include vector construction, vector transformation, protein induction expression, bacteria collection, protein purification, activity assay, etc. The mutant-type RNase R provided by the present invention improves the expression yield and salt tolerance of RNase R and is beneficial to meeting diverse RNA sample requirements.

5 Claims, 5 Drawing Sheets

Specification includes a Sequence Listing.

FIG. 1

MUTANT-TYPE RNase R, AND PREPARATION METHOD THEREFOR AND APPLICATION THEREOF

CROSS-REFERENCE TO RELATED APPLICATIONS

The application claims priority to Chinese patent application No. 2022101087308, filed on Jan. 28, 2022, the entire contents of which are incorporated herein by reference.

SEQUENCE LISTING

The sequence listing xml file submitted herewith, named "MUTANT_TYPE_RNASE_R_AND_PREPARATION_METHOD_THEREFOR_AND_APPLICATION_THEREOF", created on Jan. 31, 2024, and having a file size of 24,576 bytes, is incorporated by reference herein.

TECHNICAL FIELD

The present invention relates to the field of molecular biology, and in particular, to a mutant-type RNase R and a preparation method therefor and application thereof.

BACKGROUND

RNase R (Ribonuclease R), with a molecular weight of about 91.4 kDa, is a 3'-5' exoribonuclease derived from the E. coli RNR superfamily, and RNA can be cleaved stepwise in the 3'-5' direction into dinucleotide and trinucleotide. RNase R can digest almost all linear RNA molecules but is not prone to digesting circular RNAs (circRNAs), lariat RNAs, and RNAs with double-stranded ends.

Currently, RNase R is commonly used for studies on the enrichment and identification of circRNAs. High-throughput sequencing is the fastest method to detect circRNAs in large batches, but traditional whole transcriptome sequencing can only detect circRNAs with high abundance and is unable to detect circRNAs with low abundance. However, by adding an additional step of RNase R digestion (RNase R+) to the whole transcriptome sequencing method, circRNAs can be relatively enriched and junction reads from the circRNAs can be enriched five- to tenfold more than those of "RNase R-" samples, thereby greatly increasing the amount of circRNA detected. In addition, with the emergence of RNA vaccines, circRNAs are also listed as an RNA vaccine candidate molecule with great research potential by various biomedical companies, and RNase R is expected to become one of the important raw materials for the large-scale preparation and purification of circRNAs. Moreover, RNase R is also commonly used by researchers in the relevant field for the identification of circRNAs and lariat RNAs.

The reaction conditions of RNase R are generally 37° C. and 10-30 min, and the reaction system requires a low NaCl concentration. When the concentration of NaCl in the reaction system is higher than 100 mM, the activity of RNase R will be significantly inhibited. Such limitations of conditions place higher requirements for the purity of RNA samples and also increase the preparation cost and loss of RNAs.

Therefore, there is an urgent need to develop a salt-tolerant RNase R mutant with a high protein expression yield.

SUMMARY

In view of the foregoing common defects in the prior art, the present invention provides a mutant-type RNase R and a preparation method and application thereof. The mutant-type RNase R provided by the present invention improves the expression yield and salt tolerance of RNase R and is beneficial to meeting diverse RNA sample requirements.

To achieve the above objectives, a technical solution adopted by the present invention is:

a mutant-type RNase R, wherein an amino acid sequence of the mutant-type RNase R- is shown as SEQ ID NO. 5.

Preferably, a nucleotide sequence encoding the amino acid sequence of the mutant-type RNase R is shown as SEQ ID NO.6.

Preferably, the amino acid sequence is obtained by site-directed mutation of an amino acid sequence of E. coli-derived wild-type RNase R; and the amino acid sequence of the E. coli-derived wild-type RNase R is shown as SEQ ID NO. 1.

Preferably, a nucleotide sequence encoding the amino acid sequence of the E. coli-derived wild-type RNase R is shown as SEQ ID NO. 2.

Preferably, the site-directed mutation is obtained by truncation mutation of #601 to #608 amino acids of the amino acid sequence of the E. coli-derived wild-type RNase R.

The present invention further provides a method for preparing the mutant-type RNase R, comprising:

S1: constructing a vector containing a nucleotide sequence encoding the mutant-type RNase R;

S2: transforming the vector obtained in the step S1 to expression strain BL21 E. coli cells to obtain an expression strain;

S3: culturing expandedly the expression strain obtained in the step S2 and performing protein induction expression;

S4: collecting the expandedly cultured expression strain and performing washing and lysis;

S5: performing protein purification; and

S6: performing protein activity assays.

Preferably, a process of constructing the vector in the step S1 is as follows:

(1) perform amino acid sequence alignment of E. coli-derived wild-type RNase R with RNase R derived from a salt-tolerant Psychrobacter sp. strain ANT206, identify amino acid residues having a significant effect on salt tolerance, and perform truncation mutation on the amino acid residues to obtain an amino acid sequence shown as SEQ ID NO. 5;

(2) amplify a nucleotide sequence encoding the mutant-type RNase R by using a PCR technique with RNase R-F/RNase R_ΔM8-R, and RNase R_ΔM8-F/RNase R-R as primers respectively, and a plasmid containing an E. coli-derived RNase R-WT gene as a template to obtain a PCR product;

(3) separate the PCR product obtained in the step (2) by agarose gel electrophoresis and then perform gel cutting and purification to obtain two DNA fragments;

(4) subject a pET21a vector after NdeI/XhoI digestion to a homologous recombination reaction with the DNA fragments obtained in the step (3), and gently and uniformly mix a reaction solution with a cloning strain Trans1-T1 Phage Resistant Chemically Competent Cell to obtain a mixed solution; and (5) place the mixed solution obtained in the step (4) in a low-temperature ice bath for 3 min, in a water bath at 42° C. for heat shock for 30 s, and then immediately in an ice bath for 2 min in order, add 200 uL of LB culture solution, spread a mixture thereof on a flat plate containing ampicillin, perform overnight cultivation at 37° C., pick 3 single clones on the next day, and perform sequencing for verification.

Preferably, a sequence of the primer RNase R-F in the step (2) is shown as SEQ ID NO. 9, and a sequence of the primer RNase R_ΔM8-R is shown as SEQ ID NO. 10; a sequence of the primer RNase R_ΔM8-F is shown as SEQ ID NO. 11; and a sequence of the primer RNase R-R is shown as SEQ ID NO. 12.

Preferably, the low temperature in the step (5) is −20° C.

The present invention further provides an application of the mutant-type RNase R in circRNA and lariat RNA identification.

It should be noted that since the same amino acid may be determined by a variety of different codons, the nucleotide sequence encoding the above mutant-type RNase R is not limited to the sequence shown as SEQ NO. 5, but may be a nucleotide sequence which is obtained by codon optimization with the nucleotide sequence shown as SEQ NO. 5 and can encode the same amino acid sequence.

Compared to the prior art, the present invention has the following technical advantages: the mutant-type RNase R provided by the present invention has higher protein expression than the wild-type RNase R and can tolerate 150 mM of NaCl.

BRIEF DESCRIPTION OF DRAWINGS

FIG. 1 is a diagram of amino acid sequence alignment of E. coli-derived RNase R (WP_038432731, PDB ID:5XGU) with Psychrobacter sp. ANT206-derived RNase R (MK624989);

DETAILED DESCRIPTION OF THE EMBODIMENTS

The present invention is further explained below with reference to embodiments, but it should be noted that the following embodiments are only used to explain the present invention rather than to limit the present invention, and all technical solutions identical or similar to the present invention fall within the protection scope of the present invention. Where no specific techniques or conditions are noted in the embodiments, operations are performed according to conventional technical methods and content of instrument specifications in the art; and where no manufacturers are noted for reagents or instruments used herein, they are all conventional products that are commercially available.

Embodiment 1 Construction of a Mutant-Type RNase R Expression Vector

Figure 1:
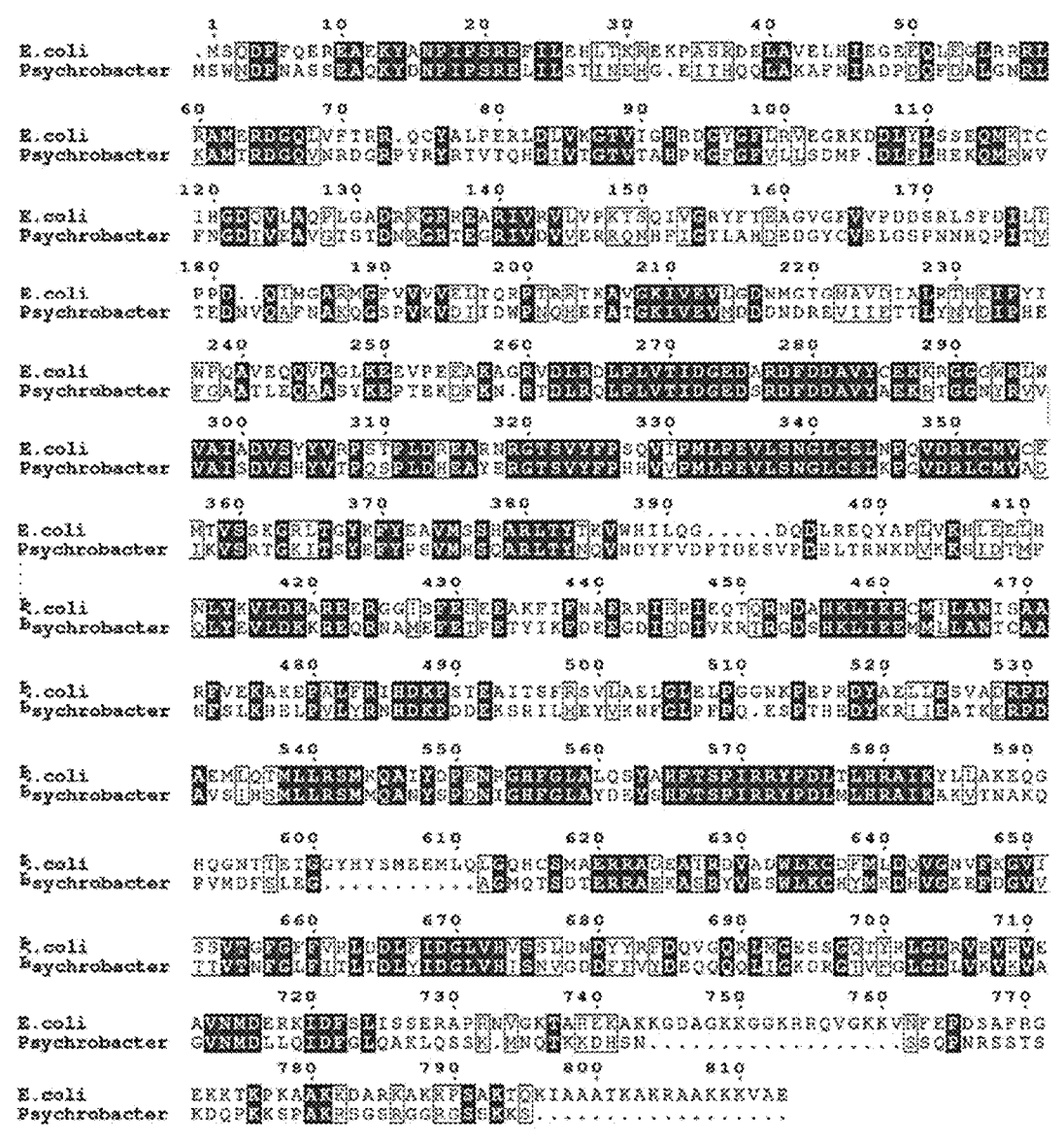

E. coli-derived wild-type RNase R (amino acid sequence shown as SEQ. NO. 1) was subjected to amino acid sequence alignment with RNase R derived from a salt-tolerant Psychrobacter sp. strain ANT206 (amino acid sequence shown as SEQ. NO. 3) (alignment results shown in FIG. 1). Amino acid residues possibly having a significant effect on salt tolerance were identified and subjected to truncation mutation, and the mutated RNase R was designated RNase R_ΔM8, the amino acid sequence of which is shown as SEQ.NO. 5.

Figure 2:
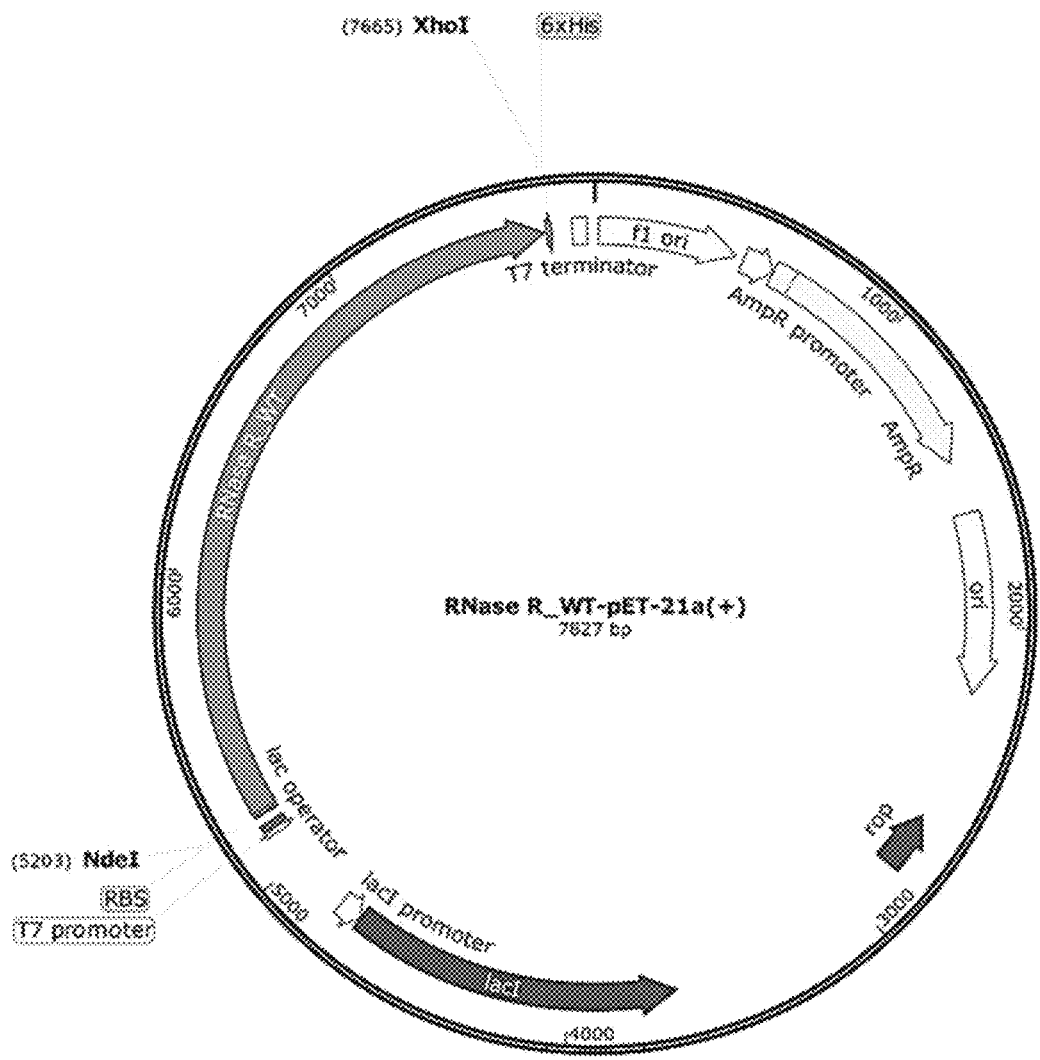
FIG. 2 is a plasmid profile of RNase R_WT-pET21a(+)

Primers were designed according to mutation points, the sequences of which are as follows:

RNase R-F: TAACTTTAAGAAGGAGATATACATATG-CATCATCATCATCATCATTCACAAG (SEQ.ID NO.9);

RNase R_ΔM8-R: TGCCGGTTTCAGTGGTGTTG-CCCTG (SEQ.NO.10);

RNaseR_ΔM8-F: GCAACACCACTGAAACCGG-CATGCTGCAACTGGGTCAGCAC (SEQ. NO.11);

RNase R-R: TCAGTGGTGGTGGTGGTGGTGCT-CGAGTCACTCTGCCACTTTTTTCTTCG (SE-Q.NO.12);

A modified RNase R_ΔM8 gene (sequence shown as SEQ ID NO. 6) was amplified by PCR, and fragments 1843 bp and 665 bp were amplified respectively with RNase R-F/RNase R_ΔM8-R and RNase R_ΔM8-F/RNase R-R as primers respectively and a plasmid containing an E. coli-derived RNase R-WT gene (shown in FIG. 2) as a template. Here, a KOD One™ PCR Master Mix-Blue (TOYOBO, article number: KMM-201) kit was used for reagent preparation during the PCR process, and the PCR amplification conditions were as follows: denaturation at 98° C. for 10 s, annealing at 58° C. for 5 s, extension at 68° C. for 2 s and a cycle number of 40.

After the above PCR product was separated by agarose gel electrophoresis, gel cutting and purification were performed by cutting off gel containing target DNAs and then purifying the DNAs using an agarose gel DNA extraction mini kit (Magen, article number: D2111-03). The two DNA fragments obtained after purification were subjected to a homologous recombination reaction with a pET21a(+) vector after NdeI/XhoI digestion through the Hieff Clone® Plus One Step Cloning Kit (Yesean, article number: 10911ES20). Here, the process of NdeI/XhoI digestion of the pET21a(+) vector was carried out as follows: 30 μL of a digestion system containing 3 μg of pET21a(+) plasmids, 3 μL of 10× FastDigest Green Buffer, 1.5 μL of FastDigest NdeI, 1.5 μL of FastDigest XhoI, and $H_2O$ complementing to 30 μL was prepared and uniformly mixed by vortexing, and then subjected to a reaction at 37° C. for 2 h.

10 μL of the reaction solution was gently and uniformly mixed with 50 μL of cloning strain Trans1-T1 Phage Resistant Chemically Competent Cell (TransGen, article number: CD501-02), a mixture thereof was placed in a low-temperature ice bath for 3 min, in a water bath at 42° C. for heat shock for 30 s, and then immediately in an ice bath for 2 min in order, 200 μL of LB culture solution was added, and a mixture thereof was spread on a flat plate containing ampicillin. After overnight cultivation at 37° C., 3 single clones were picked on the next day, and sequencing was performed for verification.

The cloned strain whose sequencing result conformed to SEQ NO. 6 was designated RNase R_ΔM8 (Trans1-T1), inoculated into 500 μL of LA culture solution, and then subjected to shaking culture at 37° C. for 5 h; 500 μL of 50% sterile glycerol was added; and a mixture thereof was stored at −80° C. after uniform mixing.

10 μL of the glycerol stock obtained above was inoculated into 5 mL of LA culture solution, overnight shock was performed at 37° C., plasmids were extracted on the next day using Hi Pure Plasmid EF Mini Kit (Magen, article number: P1111-03), and the obtained plasmids were RNase R_ΔM8-pET21a(+) vectors. 100 ng of RNase R_ΔM8-pET21a(+) plasmids were used for transforming E. coli BL21 (DE3) by a heat shock method to obtain a protein expression strain RNase R_ΔM8(BL21(DE3)), and the expression strain was also stored by adding glycerol.

Embodiment 2 Protein Expression

The expression strain RNase R_ΔM8(BL21(DE3)) obtained in the Embodiment 1 was inoculated into 5 mL of LA culture solution and placed in a 200 rpm shaker at 37° C. for overnight shaking culture.

On the next day, 5 mL of the overnight culture was inoculated into 500 mL of new LA culture solution and cultivated in a 200 rpm shaker at 37° C. for 3 h (OD value: about 0.5), 500 μL of IPTG (1 M) was added into the culture solution (final concentration: 1 mM), and shaking cultivation was further performed in a 200 rpm shaker at 37° C. for 3 h. The shaken culture was centrifuged at 10,000 g for 5 min to collect bacteria and washed once with 5 mL of sterile PBS.

Embodiment 3 Protein Purification 40 mL of equilibrium wash buffer (50 mM of phosphate, 500 mM of NaCl, 20 mM of imidazole, 0.05% Tween 20, 10% Glycerol, pH 8.0) was added to the bacteria collected in the Embodiment 2, vortexing was performed until the bacteria were sufficiently resuspended, the centrifuge tube was fixed in an ice water bath and an ultrasonic probe was inserted 1-2 cm below the liquid level to conduct ultrasonic treatment (75% power, ultrasonic treatment for 4 s at an interval of 6 s, 10 min in total) until the bacteria solution was clear and transparent, the bacterial solution was centrifuged at 18,000 g at 4° C. for 60 min, and a supernatant (i.e., RNase R_ΔM8 protein lysis buffer) was transferred to a new centrifuge tube.

Protein purification was performed using a protein purification system (Unique AutoPure, Inscinstech):

Ni-NTA column purification: after the system tube and the Ni-NTA column (BBI, article number: C600792, specification of 1 mL) were flushed with DEPC treated water, the column was equilibrated with the equilibrium wash buffer. The sample was loaded at a flow rate of 0.8 mL/min, the heteroprotein was washed with the equilibrium wash buffer, and finally, an elution buffer (50 mM of phosphate, 500 mM of NaCl, 500 mM of imidazole, 0.05% Tween 20, 10% Glycerol, pH 8.0) was used for eluting and collecting the target protein.

Concentration with an ultrafiltration tube: the target protein collected above was appropriately concentrated to 2 mL using an ultrafiltration tube (Millipore, UFC805024, 50K MWCO) and a refrigerated centrifuge.

Desalting with a desalting column: after the system tube and the desalting column (GE, article number 29048684, specification of 5 mL) were flushed with DEPC treated water, the column was equilibrated with 2× storage buffer without glycerol (100 mM Tris-HCl (pH 7.5), 200 mM of NaCl, 0.2 mM of EDTA, 2 mM of DTT, 0.2% Triton® X-100). The sample was drawn and injected with a disposable syringe into a quantitative loop in a "manual loading" mode, and then passed through the column at a flow rate of 2 mL/min; the sample was collected when a protein peak appeared and sample collection was stopped when a salt peak appeared.

Figure 3:
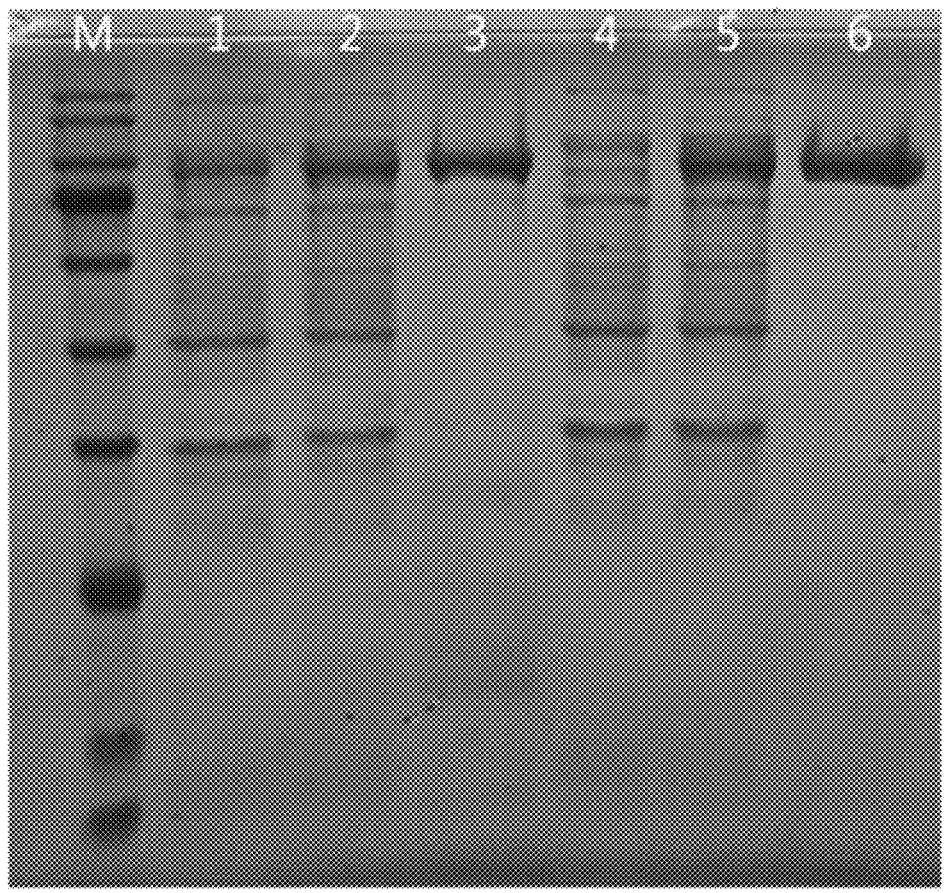
FIG. 3 is a diagram of RNase R expression and purification results detected by SDS-PAGE.

The desalted enzyme solution was added to an equal volume of glycerol, and a mixture thereof was gently and uniformly mixed by inverting and then stored in a refrigerator at −20° C. after centrifugation for a short time. Specific RNase R expression and purification conditions are shown in FIG. 3, wherein 1) represents cell lysis buffer before RNase R_WT induction; 2) represents cell lysis buffer after RNase R_WT induction by IPTG; 3) represents RNase R_WT proteins after Ni-NTA column purification; 4) represents cell lysis buffer before RNase R_ΔM8 induction; 5) represents cell lysis buffer after RNase R-M8 induction by IPTG; and 6) represents RNase R_ΔM8 proteins after Ni-NTA column purification.

Embodiment 4 Protein Quantification

Figure 4:
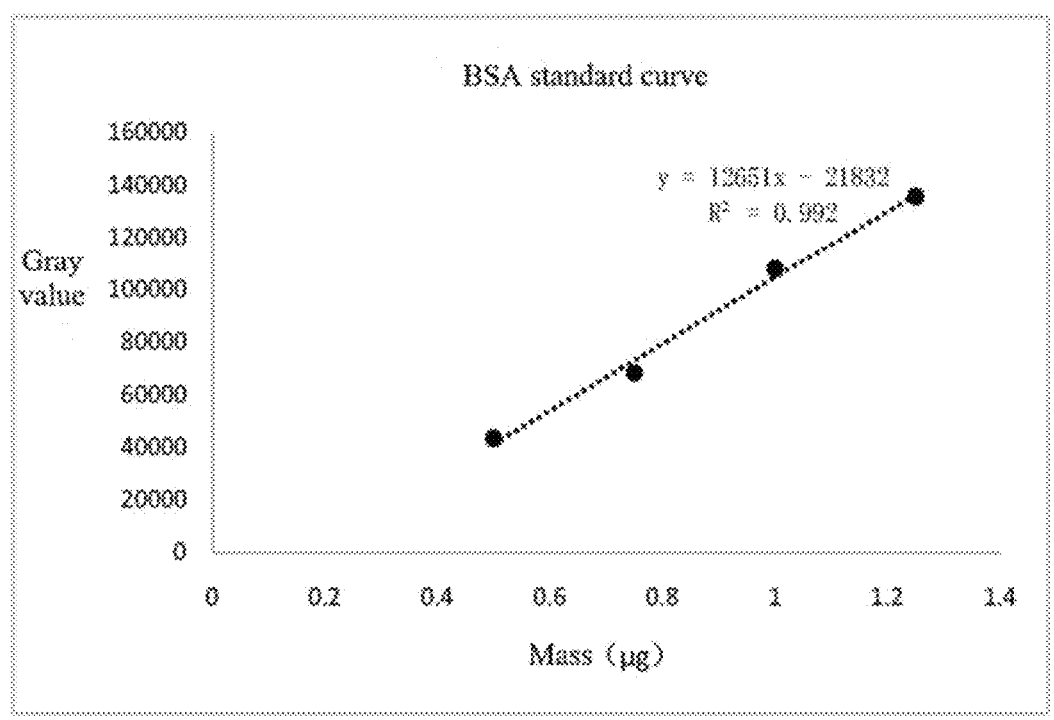
FIG. 4 is a BSA standard curve.

The obtained RNase R was subjected to SDS-PAGE simultaneously with different masses of BSA. Coomassie brilliant blue G250 staining was adopted after electrophoresis, photographs were taken after de-staining, and gray analysis was performed using Quantity One software. A standard curve was drawn with the Y axis representing gray values and the X axis representing BSA sample loading mass (shown in FIG. 4). The concentration and yield of the RNase R enzyme solution were calculated according to the BSA standard curve (shown in Table 1). The obtained enzyme solution was diluted to 1 μg/L with storage buffer and stored at −20° C.

Table 1 Comparison of Yield between Wild-type RNase R and Mutant-type RNase R

| Enzyme | Yield(μg) |
|---|---|
| RNase R_WT | 2020 |
| RNase R_ΔM8 | 2735 |

Embodiment 5 Preparation of Reaction Substrate

1) A gene synthesis method was used for synthesizing primers required for PCR, with the sequences as follows:
Linear_RNA1/2-F: 5 TAATACGACTCACTATAGG-GAAAAAAGGAGGTTTTAGTCTAGGGAAAGTCATTCA 3' (SEQ NO.13);
Linear_RNA1-R:5'TTGAAAAAATCATGAGAT-TTTCTCTCTTA 3' (SEQ NO.14);
Linear_RNA2-R:5'GGGAAAAAATCATGAGAT-TTTCTCTCTTA 3' (SEQ NO.15);

2) A DNA template was synthesized using PCR.

With a plasmid containing a circ-ACE2 RNA sequence as a template, PCR amplification was performed using Linear_RNA1/2-F (SEQ NO.13) and Linear_RNA1-R(SEQ NO.14); after the PCR product was separated by agarose gel electrophoresis, gel cutting was performed for recovery to obtain a template DNA1, and the PCR amplification process here also employed the KOD One™ PCR Master Mix-Blue- (TOYOBO, article number: KMM-201) kit for system preparation and was conducted under the following conditions: denaturation at 98° C. for 10 s, annealing at 58° C. for 5 s, extension at 68° C. for 1 s. and a cycle number of 40.

With a plasmid containing circ-ACE2 RNA sequence as a template, PCR amplification was performed using Linear_RNA1/2-F (SEQ NO.13) and Linear_RNA2-R (SEQ NO.15) (the same process as that of DNA1); after the PCR product was separated by agarose gel electrophoresis, gel cutting was performed for recovery to obtain a template DNA2.

1) In Vitro Synthesis of Linear RNA Using T7 RNA Polymerase

Linear_RNA1 (SEQ NO.7) with two complementary and paired ends but 2 bases protruding from the 3' end was synthesized by in vitro transcription using DNA1 as the template and TranscriptAid T7 High Yield Transcription Kit (Thermo Scientific, article number: K0441) to serve as the target RNA in an RNase R specific digestion reaction.

Linear_RNA2 (SEQ NO.8) with two fully complementary and paired ends was synthesized by in vitro transcription using DNA2 as the template and TranscriptAid T7 High Yield Transcription Kit (Thermo Scientific, article number: K0441) to serve as a control RNA in an RNase R specific digestion reaction.

The above RNA synthesis and purification methods are as follows:

(1) Synthesis of RNA by in vitro transcription. Linear_RNA1 and Linear_RNA2 were synthesized using DNA1 and DNA2 as templates respectively. As shown in Table 2, the reaction system was prepared in order and a reaction was allowed at 37° C. for 2 h after gentle and uniform mixing.

TABLE 2

Reaction System for In Vitro Transcription

| Component | Usage amount |
| --- | --- |
| DEPC treated water | Complementing to 20 μL |
| 5 × TranscriptAid Reaction Buffer | 4 μL |
| ATP, Tris buffered 100 mM* | 2 μL |
| UTP, Tris buffered 100 mM* | 2 μL |
| GTP, Tris buffered 100 mM* | 2 μL |
| CTP, Tris buffered 100 mM* | 2 μL |
| DNA1 or DNA2 | 1 μg |
| TranscriptAid Enzyme Mix | 2 μL |

(2) After the reaction was completed, 2 μL of DNase I (RNase-free, 1 U/μL DNA) was added to 20 μL of the system and a reaction was allowed at 37° C. for 15 min after uniform mixing, and then the DNA template was digested.

(3) The product obtained in the step (2) was transferred to an RNase-free centrifuge tube of 1.5 mL, 1 mL of Trizol was added for RNA purification, and the subsequent operation was the same as that of extracting RNA from cells with Trizol.

(4) The obtained RNA was dissolved by adding an appropriate amount of DEPC treated water, and a mixture thereof was stored in a freezer at −80° C. after concentration determination.

Embodiment 6 Assay of RNase R Activity and Salt Tolerance 1) 10× reaction buffers with different concentrations of NaCl were prepared as shown in Table 3

TABLE 3

10 × Reaction Buffers with Different Concentrations of NaCl.

| Mark number of reaction | Formulation of reaction buffer |
| --- | --- |
| 10 × buf1 | 200 mM Tris-HCl (pH 8.0), 1000 mM KCl, 1 mM |
| 10 × buf2 | 500 mM NaCl, 200 mM Tris-HCl (pH 8.0), 1000 mM |
| 10 × buf3 | 1000 mM NaCl, 200 mM Tris-HCl (pH 8.0), 1000 mM |
| 10 × buf4 | 1500 mM NaCl, 200 mM Tris-HCl (pH 8.0), 1000 mM |
| 10 × buf5 | 2000 mM NaCl, 200 mM Tris-HCl (pH 8.0), 1000 mM |
| 10 × buf6 | 3000 mM NaCl, 200 mM Tris-HCl (pH 8.0), 1000 mM |

Figure 5:
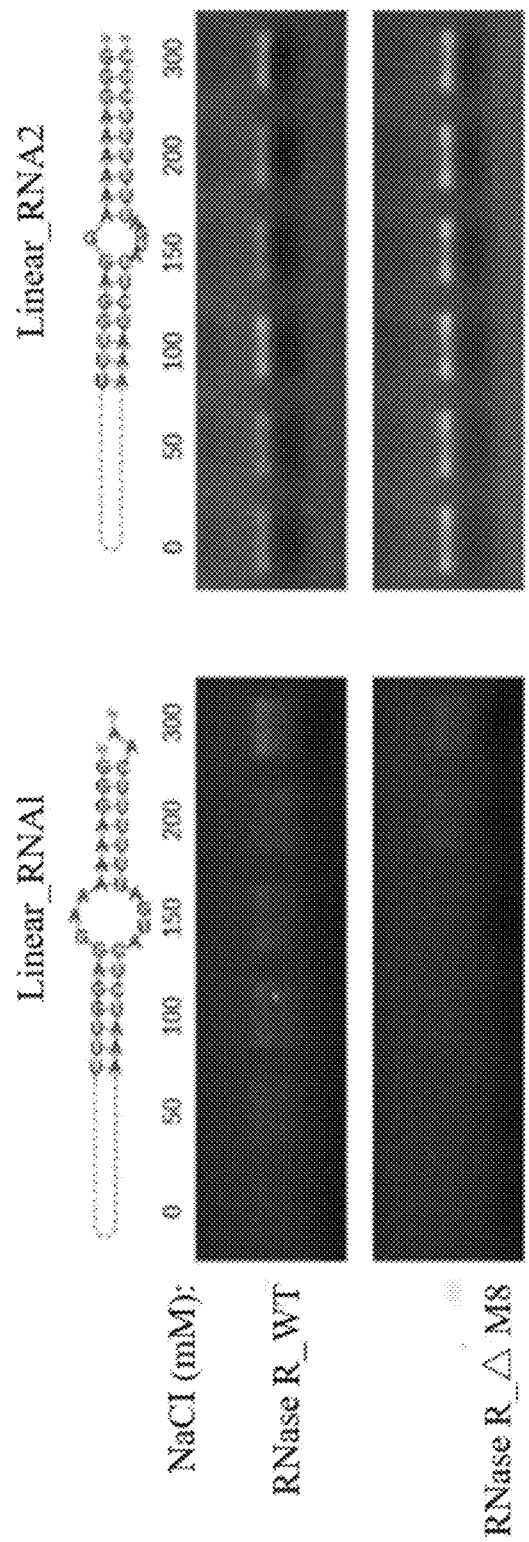
FIG. 5 is a diagram of salt tolerance detection results of RNase R_WT and RNase R_ΔM8.

2) As shown in Table 4, in a 20 μL system, 3 μg of Linear_RNA1 or Linear_RNA2 was used as the substrate, the reaction buffers with different concentrations of NaCl were added respectively, and the mutant-type RNase R(RNase R_ΔM8) was finally added; a reaction was allowed at 37° C. for 15 min after uniform mixing; heat inactivation was performed at 70° C. for 10 min; and the reaction solution was stored in an ice box. The wild-type RNase R (RNase R_WT) was used in the above test as a control. 3 μL of 2×RNA Loading Dye (NEB, article number: B0363A) was added to 3 μL of the reaction solution for 1.5% agarose gel electrophoresis. The results are shown in FIG. 5. The wild-type RNase R (RNase R_WT) and the mutant-type RNase R (RNase R_ΔM8) substantially digested little RNA2 with a fully double-stranded end structure and could digest RNA1 with a protruding structure at the 3' end. Compared to the wild-type RNase R (RNase R_WT), the mutant-type RNase R (RNase R_ΔM8) had stronger digestibility and was able to tolerate NaCl at a final concentration of 150 mM.

TABLE 4

RNase R Reaction System

| Component | Usage amount |
| --- | --- |
| DEPC treated water | Complementing to 20 μL |
| RNA | 3 μg |
| 10 × buf1/2/3/4/5/6 | 2 μL |
| RNase R(1 μg/μL) | 0.5 μL |

It should be noted that although the above embodiments have been described, those skilled in the art may make additional changes and modifications to these embodiments once they know the basic inventive concepts. Therefore, the foregoing description is merely illustrative of the embodiments of the present invention and is not intended to limit the protection scope of the present invention. Any equivalent structure or process variations based on the specification of the present invention, or direct or indirect application of these embodiments to other related technical fields all fall within the protection scope of the present invention.

What is claimed is:

1. A mutant-type RNase R, wherein an amino acid sequence of the mutant-type RNase R is shown as SEQ ID NO: 5.

2. A nucleic acid encoding the mutant-type RNase R according to claim 1, wherein a nucleotide sequence of the nucleic acid is shown as SEQ ID NO: 6.

3. A method for preparing the mutant-type RNase R according to claim 1, comprising:
S1: constructing a vector containing a nucleotide sequence encoding the mutant-type RNase R;
S2: transforming the vector obtained in the step S1 to BL21 E. coli cells to obtain an expression strain;
S3: culturing expandedly the expression strain obtained in the step S2 and performing protein induction expression;
S4: collecting the expandedly cultured expression strain and performing washing and lysis;
S5: performing protein purification; and
S6: performing protein activity assays.

4. The preparation method according to claim 3, wherein a process of the constructing a vector in the step S1 is as follows:

(1) perform amino acid sequence alignment of E. coli-derived wild-type RNase R with RNase R derived from a salt-tolerant (Psychrobacter sp.) strain ANT206, identify amino acid residues having a significant effect on salt tolerance, and perform truncation mutation on the amino acid residues to obtain an amino acid sequence shown as SEQ ID NO: 5;

(2) amplify a nucleotide sequence encoding the mutant-type RNase R using a PCR technique with RNase R-F/RNase R_ΔM8-R and RNase R_ΔM8-F/RNase R-R as primers respectively and a plasmid containing an E. coli-derived RNase R-WT gene as a template to obtain a PCR product;

(3) separate the PCR product obtained in the step (2) by agarose gel electrophoresis and then perform gel cutting and purification to obtain two DNA fragments;

(4) subject a pET21a vector after NdeI/XhoI digestion to a homologous recombination reaction with the DNA fragments obtained in the step (3), and gently and uniformly mix a reaction solution with a cloning strain Trans1-T1 Phage Resistant Chemically Competent Cell to obtain a mixed solution;

(5) place the mixed solution obtained in the step (4) in a low-temperature ice bath for 3 min, in a water bath at 42° C. for heat shock for 30 s, and then immediately in an ice bath for 2 min, add 200 uL of LB culture solution, spread a mixture thereof on a flat plate containing ampicillin, perform overnight cultivation at 37° C., pick 3 single clones on the next day, and perform sequencing for verification, wherein a sequence of the primer RNase R-F in step (2) is shown as SEQ ID NO: 9, and a sequence of the primer RNase R_ΔM8-R is shown as SEQ ID NO; 10; a sequence of the primer RNase R_ΔM8-F is shown as SEQ ID NO: 11; and a sequence of the primer RNase R-R is shown as SEQ ID NO: 12.

5. The preparation method according to claim 4, wherein the low temperature in the step (5) is −20° C.

* * * * *

SEQUENCE LISTING

```
Sequence total quantity: 15
SEQ ID NO: 1             moltype = AA    length = 813
FEATURE                  Location/Qualifiers
source                   1..813
                         mol_type = protein
                         organism = synthetic construct
SEQUENCE: 1
MSQDPFQERE AEKYANPIPS REFILEHLTK REKPASRDEL AVELHIEGEE QLEGLRRRLR    60
AMERDGQLVF TRRQCYALPE RLDLVKGTVI GHRDGYGFLR VEGRKDDLYL SSEQMKTCIH   120
GDQVLAQPLG ADRKGRREAR IVRVLVPKTS QIVGRYFTEA GVGFVVPDDS RLSFDILIPP   180
DQIMGARMGF VVVVELTQRP TRRTKAVGKI VEVLGDNMGT GMAVDIALRT HEIPYIWPQA   240
VEQQVAGLKE EVPEEAKAGR VDLRDLPLVT IDGEDARDFD DAVYCEKKRG GGWRLWVAIA   300
DVSYYVRPST PLDREARNRG TSVYFPSQVI PMLPEVLSNG LCSLNPQVDR LCMVCEMTVS   360
SKGRLTGYKF YEAVMSSHAR LTYTKVWHIL QGDQDLREQY APLVKHLEEL HNLYKVLDKA   420
REERGGISFE SEEAKFIFNA ERRIERIEQT QRNDAHKLIE ECMILANISA ARFVEKAKEP   480
ALFRIHDKPS TEAITSFRSV LAELGLELPG GNKPEPRDYA ELLESVADRP DAEMLQTMLL   540
RSMKQAIYDP ENRGHFGLAL QSYAHFTSPI RRYPDLTLHR AIKYLLAKEQ GHQGNTTETG   600
GYHYSMEEML QLGQHCSMAE RRADEATRDV ADWLKCDFML DQVGNVFKGV ISSVTGFGFF   660
VRLDDLFIDG LVHVSSLDND YYRFDQVGQR LMGESSGQTY KGDRVEVRV EAVNMDERKI   720
DFSLISSERA PRNVGKTARE KAKKGDAGKK GGKRRQVGKK VNFEPDSAFR GEKKTKPKAA   780
KKDARKAKKP SAKTQKIAAA TKAKRAAKKK VAE                                813

SEQ ID NO: 2             moltype = DNA    length = 2442
FEATURE                  Location/Qualifiers
source                   1..2442
                         mol_type = other DNA
                         organism = synthetic construct
SEQUENCE: 2
atgtcacaag atcctttcca ggaacgcgaa gctgaaaaat acgcgaatcc catccctagt    60
cgggaattta tcctcgaaca tttaaccaaa cgtgaaaaac cggccagccg tgatgagctg   120
gcggtagaac tgcacattga aggcgaagag cagcttgaag gcctgcgtcg ccgcctgcgc   180
gcgatggagc gcgatggtca actggtcttc actcgtcgtc agtgctatgc gctgccggaa   240
cgcctcgacc tggtgaaagg taccgttatt ggccaccgtg atggctacgg ctttctgcgg   300
gttgaagggc gtaaagatga tttgtatctc tccagcgagc agatgaaaac ctgcattcat   360
ggcgatcagg tgctggcgca gccgctgggc gctgaccgta aggtcgtcg tgaagcgcgt   420
attgtccgcg tactggtgcc aaaaaccagc cagattgtcg gtcgctactt tactgaagcg   480
ggcgtcggct ttgtggttcc tgacgatagc cgtctgagct tcgatatctt aatcccgccc   540
gatcagatca tgggcgcgag gatgggcttt gtggtcgtag tcgaactgac tcagcgtccg   600
actcgccgca ccaaagcggt gggtaaaatc gtcgaagtgc tgggcgacaa tatgggcacc   660
ggcatggcgg ttgatatcgc tctcgatgcc catgaaattc cgtacatctg gccgcaggct   720
gttgagcaac aggttgccgg gctgaaagaa gaagtgccgg aagaagcaaa agcgggccgt   780
gttgatctgc gcgatttacc gctggtcacc attgatggcg aagacgcccg tgactttgac   840
gatgcagttt actgcgagaa aaaacgcggc ggcggctggc gtttatgggt cgcgattgcc   900
gacgtcagct actatgtgcg tccgtcaacg ccgctgacga gagaagcgta taaccgtggc   960
acgtcggtgt acttcccttc gcaggttatc ccgatgctgc cggaagtgct ctctaacggc  1020
ctgtgttcgc tcaacccgca ggtagaccgc ctgtgtatgg tgtgcgagat gacggtttcg  1080
tcgaaaggcc gcctgacggg ctacaaattc tacgaagcgg tgatgagctc tcacgcgcgt  1140
ctgacctaca ccaaagtctg gcatattctg cagggcgatc aggatctgcg cgagcagtac  1200
gccccgctgg ttaagcatct cgaagagttg cataacctct ataaagtgct ggataaagcc  1260
cgtgaagaac gcggtgggat ctcatttgag agcgaagaag cgaagttcat tttcaacgct  1320
gaacgccgta ttgaacgtat cgaacagacc cagcgtaacg acgcgcacaa attaattgaa  1380
gagtgcatga ttctggcgaa tatctcggcg gcgcgtttcg ttgagaaagc gaaagaaccg  1440
gcactgttcc gtattcacga caagccgagc accgaagcga ttacctcttt ccgttcagtg  1500
ctggcggagc tggggctgga actgccgggc ggtaacaagc cggaaccgcg tgactacgcg  1560
gagctgctgg agtcggttgc cgatcgtcct gatgcagaaa tgctgcaaac catgctgctg  1620
cgctcgatga acaggcgat ttacgatcca gaaaaccgtg gtcactttgg cctggcattg  1680
cagtcctatg cgcactttac ttcgccgatt cgtcgttatc cagacctgac gctgcaccgc  1740
gccattaaat atctgctggc gaaagagcag gggcatcagg gcaacaccac tgaaaccggc  1800
ggctaccatt attcgatgga agagatgctg caactgggtc agcactgttc gatgcggaa   1860
cgtcgtgccg acgaagcaac gcgcgatgtg gctgactggc tgaagtgtga cttcatgctc  1920
gaccaggtag gtaacgtctt taaaggcgta atttccaggc tcactggctt tggcttcttc  1980
gtccgtctgg acgacttgtt cattgatggt ctggtccatg tctcttcgct ggacaatgac  2040
tactatcgct ttgaccaggt agggcaacgc ctgatggggg aatccagcgg ccagacttat  2100
cgcctggcg atcgcgtgga agttcgcgtc gaagcggtta atatgacga gcgcaaaatc  2160
gactttagcc tgatctccag cgaacgcgca ccgcgcaacg tcggtaaaac ggcgcgcgag  2220
aaagcgaaaa aaggcgatgc aggtaaaaaa ggcggcaagc gtcgtcaggt cggtaaaaag  2280
gtaaactttg agccagacag cgccttccgc ggtgagaaaa aaacgaagcc gaaagcggcg  2340
aagaagacg cgagaaaagc gaaaaagcca tcggcgaaaa cgcagaaaat agctgcagcg  2400
accaaagcga agcgtgcggc gaagaaaaaa gtggcagagt ga                      2442

SEQ ID NO: 3             moltype = AA    length = 770
FEATURE                  Location/Qualifiers
source                   1..770
                         mol_type = protein
                         organism = synthetic construct
SEQUENCE: 3
MSWNDPNASS EAQKYDNPIP SRELILSTIN EHGEITHQQL AKAFNIADPD QFDALGNRLK    60
AMTRDGQVNR DGRPYRYRTV TQHDIVTGTV TAHPKGFGFV LLSDMPDLFL HEKQMRWVFN   120
```

```
GDTVEAVGTS TDNRGRTEGR IVDVVERRQN HFIGTLAHDE DGYCVELGSP NNHQPITVTE    180
DNVQAFNAKQ GSPVKVDIID WPNQHEFATG KIVEVMDDDN DREVIIETTL YNYDIPHEFG    240
AATLEQAASY KEPTEKDFKN RTDLRQLPLV TIDGEDSRDF DDAVYAEKRT GGNYRVVVAI    300
SDVSHYVTPQ SPLDHEAYER GTSVYFPHHV VPMLPEVLSN GLCSLKPGVD RLCMVADIKV    360
SRTGKITSYE FYPSVMHSQA RLTYNQVNDY FVDPTDESVP DELTRNKDVK KSIDTMFQLY    420
EVLDKKREQR NAMEFETPET YIKFDEEGDI DDIVKRTRGD SHKLIEEMML LANTCAANFS    480
LKHELPVLYR NHDKPDDEKS RILHEYVKNF GLPFPQESPT HEDYKRIIEA TKERPDAVSI    540
HSMLLRSMMQ ANYSPDNIGH FGLAYDEYSH FTSPIRRYPD LMLHRAIKAK VTNAKQPVMD    600
FSLEGAGMQT SDTERRAEKA SRYVESWLKC HYMKDHVGEE FDGVVTTVTN FGLFITLTDL    660
YIDGLVHISN VGDDFFVYDE QQQQLIGKDR GTVFGLGDLV KVKVAGVNMD LLQIDFGLQA    720
KLQSSKMNQT KKDHSNSSQP NRSSTSKDQP KKSPAKRSGS RGGRGSSKKS               770

SEQ ID NO: 4              moltype = DNA  length = 2313
FEATURE                   Location/Qualifiers
source                    1..2313
                          mol_type = other DNA
                          organism = synthetic construct
SEQUENCE: 4
atgagttgga atgatccaaa cgcctcaagt gaggcacaaa aatatgataa cccgattcct     60
agtcgcgagc ttatattaag cacgattaat gaacacggtg aaatcaccca tcagcaattg    120
gcaaaagcct ttaatattgc tgatcccgat cagtttgacg ctttaggcaa ccgcctaaaa    180
gcgatgacac gcgatggaca agtcaatcgt gacggtcgtc cttatcgctca tcgtacggtc    240
actcagcacg acatcgtcac cggtacagta acagcccatc caaagggctt tggcttgta    300
ttattaagtg atatgcctga cctattcttg catgaaaaac aaatgcgttg ggtctttaat    360
ggcgatacag tagaagccgt tggcacgtca acagacaacc gcggtcgtac tgaaggtcgt    420
atcgttgatg tcgttgagcg tcgtcaaaat catttttatcg gtacgctgtc tcatgatgaa    480
gacggttact gcgttgagct tggtagccca aataaccatc agccgattac cgttacagaa    540
gacaatgtac aggcttttcaa tgctaagcaa ggctcgccgg taaaagttga tattattgat    600
tggccaaatc agcatgaatt tgccacgggc aaaatcgttg aagtcatgga tgatgacaat    660
gatcgcgaag taatcattga gactacgtta tataattatg atattccaca tgagttcgat    720
gccgcgactc tcgagcaagc agcttctgtat aaagagccga ctgaaaaaga tttcaaaaat    780
cgtactgact acgtcaatt gccattagtg acgatcgatg gtgaagattc ccgtgacttt    840
gatgatgctg tgtatgcaga aaagcgtaca ggtggtaatt atcgcgtcgt ggtagcgatt    900
agtgatgtca gtcattgt gacaccgcag tcgccacttg atcacgaagc ctacgagcgt    960
ggtacgtcag tatatttccc gcatcatgtg gtgcctatgt tgcctgaagt actgtctaat   1020
ggtctctgtt cgctgaagcc tggcgtcgat cgcctctgta tggttgctga tattaaggta   1080
tcacgtacag gtaaaatcac cagttatgag ttttatccta gtgtcatgca ctcgcaagcg   1140
cgcttgactt acaataagt gaacgattat tttgtagatc caactgacga gagcgttcca   1200
gacgaattga caagaaataa agacgtcaaa aaatccatgt ccaactgtat   1260
gaggtactcg ataaaagcg tgaacaacgt aacgcgatgg agtttgagac cccagaaact   1320
tatattaagt tcgatgaaga aggtgatatc gatgatatcg taaagcgtac gcgcggtgat   1380
tcacataagc ttatcgaaga tgatgatgttg cttgccaata cctgtgcagc aaactttttca   1440
ctaaaacacg agctgcctgt gttatatcgt aatcatgata agcctgatga tgaaaagtcg   1500
agaatttttac atgaatatgt caaaaacttt ggtctaccct tcccacagga aagtcctact   1560
cacgaggatt ataaacgtat cattgaagca actaaagagc gaccggatgc ggttagcatt   1620
catagcatgc tgcttcgttc gatgatgcaa gcgaactatt cacctgacaa tatcggtcac   1680
tttggtttgg cttacgatga gtatagtcat ttcacctcgc cgattcgtcg ttatcctgac   1740
ttaatgttgc atcgtgcgat caaggcgaaa gtgacaaatg ccaaacagcc tgtgatggat   1800
ttttcattag aaggtgctgg catgcaaacc tcagatactg agcgccgtgc tgaaaaggct   1860
tcacgctacg tagaatcatg gctcaaatgt cattatatga aagatcatgt cggcgaagag   1920
ttcgatggtg tcgtaactac cgtcacaaac tttggttttat ttattactct gacggatttg   1980
tatatcgatg gtttggtgca tatctcaaac gttggtgacg atttctttgt ttatgatgag   2040
cagcagcaac agcttatcgg taaagataga ggcacagtgt ttgggctggg cgatttggtt   2100
aaagttaaag tagctggcgt taatatggat ctgctacaaa ttgactttgg tttacaagca   2160
aagctgcaat ctagtaaaat gaatcaaact aagaaagatc attcaaactc tagtcagcca   2220
aaccgcagct ccacaagcaa agatcagcca agaaatcac ctgcgaagag aagcggcagt   2280
cgtggtggta gaggcagtag taaaagagc taa                                 2313

SEQ ID NO: 5              moltype = AA  length = 805
FEATURE                   Location/Qualifiers
source                    1..805
                          mol_type = protein
                          organism = synthetic construct
SEQUENCE: 5
MSQDPFQERE AEKYANPIPS REFILEHLTK REKPASRDEL AVELHIEGEE QLEGLRRRLR     60
AMERDGQLVF TRRQCYALPE RLDLVKGTVI GHRDGYGFLR VEGRKDDLYL SSEQMKTCIH    120
GDQVLAQPLG ADRKGRREAR IVRVLVPKTS QIVGRYFTEA GVGFVVPDDS RLSFDILIPP    180
DQIMGARMGF VVVVELTQRP TRRTKAVGKI VEVLGDNMGT GMAVDIALRT HEIPYIWPQA    240
VEQQVAGLKE EVPEEAKAGR VDLRDLPLVT IDGEDARDFD DAVYCEKKRG GGWRLWVAIA    300
DVSYYVRPST PLDREARNRG TSVYFPSQVI PMLPEVLSNG LCSLNPQVDR LCMVCEMTVS    360
SKGRLTGYKF YEAVMSSHAR LTYTKVWHIL QGDQDLREQY APLVKHLEEL HNLYKVLDKA    420
REERGGISFE SEEEAKIFNA ERRIERIEQT QRNDAHKLIE ECMILANISA ARFVEKAKEP    480
ALFRIHDKPS TEAITSFRSV LAELGLELPG GNKPEPRDYA ELLESVADRP DAEMLQTMLL    540
RSMKQAIYDP ENRGHFGLAL QSYAHFTSPI RRYPDLTLHR AIKYLLAKEQ GHQGNTTETG    600
MLQLGQHCSM AERRADEATR DVADWLKCDF MLDQVGNVFK GVISSVTGFG FFVRLDDLFI    660
DGLVHVSSLD NDYYRFDQVG QRLMGESSGQ TYRLGDRVEV RVEAVNMDER KIDFSLISSE    720
RAPRNVGKTA REKAKKGDAG KKGGKRRQVG KKVNFEPDSA FRGEKKTKPK AAKKDARKAK    780
KPSAKTQKIA AATKAKRAAK KKVAE                                         805
```

```
SEQ ID NO: 6              moltype = DNA  length = 2418
FEATURE                   Location/Qualifiers
source                    1..2418
                          mol_type = other DNA
                          organism = synthetic construct
SEQUENCE: 6
atgtcacaag atcctttcca ggaacgcgaa gctgaaaaat acgcgaatcc catccctagt    60
cgggaattta tcctcgaaca tttaaccaaa cgtgaaaaac cggccagccg tgatgagctg   120
gcggtagaac tgcacattga aggcgaagag cagcttgaag gcctgcgtcg ccgcctgcgc   180
gcgatggagc gcgatggtca actggtcttc actcgtcgtc agtgctatgc gctgccggaa   240
cgcctcgacc tggtgaaagg taccgttatt ggccaccgtg atggctacgg cttttctgcg   300
gttgaagggc gtaaagatga tttgtatctc tccagcgagc agatgaaaac ctgcattcat   360
ggcgatcagg tgctggcgca gccgctgggc gctgaccgta aaggtcgtcg tgaagcgcgt   420
attgtccgcg tactggttgcc aaaaaccagc cagattgttg gtcgctactt tactgaagcg   480
ggcgtcggct ttgtggttcc tgacgatagc cgtctgagct tcgatatctt aatcccgccc   540
gatcagatca tgggcgcgag gatgggcttt gtggtcgtag tcgaactgac tcagcgtccg   600
actcgccgca ccaaagcggt gggtaaaatc gtcgaagtgc tgggcgacaa tatgggcacc   660
ggcatggcgg ttgatatcgc tctgcatacc catgaaattc cgtacatctg gccgcaggct   720
gttgagcaac aggttgccgg gctgaaagaa gaagtgccgg aagaagcaaa agcgggccgt   780
gttgatctgc gcgatttacc gctggtcacc attgatggcg aagacgcccg tgactttgac   840
gatgcagttt actgcgagaa aaaacgcggc ggcggctggc gtttatgggt cgcgattgcc   900
gacgtcagct actatgtgcg tccgtcaacg ccgctgacga agaagcgcta taaccgtcgc   960
acgtcggtgt acttcccttc gcaggttatc ccgatgctgc cggaagtgct ctctaacggc  1020
ctgtgttcgc tcaacccgca ggtagaccgc ctgtgtatgg tgtgcgagat gacggtttcg  1080
tcgaaaggcc gcctgacggg ctacaaattc tacgaagcgg tgatgagctc tcacgcgcgt  1140
ctgacctaca ccaaagtctg gcatattctg cagggcgatc aggatctgcg cagcagtac   1200
gccccgctgg ttaagcatct cgaagagttg cataacctct ataaagtgct ggataaagcc  1260
cgtgaagaac gcggtgggat ctcatttgag agcgaagaag cgaagttcat ttcaacgct   1320
gaacgccgta ttgaacgtat cgaacagacc cagcgtaacg acgcgcacaa attaattgaa  1380
gagtgcatga ttctggcgaa tatctcggcg gcgcgttcg ttgagaaagc gaaagaaccg  1440
gcactgttcc gtattcacga caagccgagc accgaagcga ttacctcttt ccgttcagtg  1500
ctggcggagc tggggctgga actgccgggc ggtaacaagc cggaaccgcg tgactacgcg  1560
gagctgctgg agtcggttgc cgatcgtcct gatgcagaaa tgctgcaaac catgctgctg  1620
cgctcgatga aacaggcgat ttacgatcca gaaaaacgtg gtcactttgg cctggcattg  1680
cagtcctatg cgcactttac ttcgccgatt cgtcgttatc cagacctgac gctgcaccgc  1740
gccattaaat atctgctggc gaaagagcag gggcatcagg gcaacaccac tgaaaccggc  1800
atgctgcaac tgggtcagca ctgttcgatg gcggaacgtc gtgccgacga agcaacgcgc  1860
gatgtggctg actggctgaa gtgtgacttc atgctcgacc aggtaggtaa cgtctttaaa  1920
ggcgtaattt ccagcgtcac tggctttggc ttcttcgtcc gtctgacga cttgttcatt  1980
gatggtctgg tccatgtctc ttcgctggac aatgactact atcgctttga ccaggtaggg  2040
caacgcctga tggggaatc cagcggccag acttatcgcc tgggcgatcg cgtcggaagtt  2100
cgcgtcgaag cggttaatat ggacgagcgc aaaatcgact ttagcctgat ctccagcgaa  2160
cgcgcaccgc gcaacgtcgg taaaacggcg cgcgagaaag cgaaaaaagg cgatcagggt  2220
aaaaaaggcg gcaagcgtcg tcaggtcggt aaaaaggtaa actttgagcc agacagcgcc  2280
ttccgcggtg agaaaaaaac gaagccgaaa gcggcgaaga agacgcgag aaaagcgaaa  2340
aagccatcgg cgaaaacgca gaaaatagct gcagcgacca aagcgaagcg tgcggcgaag  2400
aaaaaagtgg cagagtga                                                2418

SEQ ID NO: 7              moltype = RNA  length = 307
FEATURE                   Location/Qualifiers
source                    1..307
                          mol_type = other RNA
                          organism = synthetic construct
SEQUENCE: 7
gggaaaaaag gaggttttag tctagggaaa gtcattcagt ggatgtgatc ttggctcaca    60
ggggacgatg tcaagctctt cctggctcct tctcagcctt gttgctgtaa ctgctgctca   120
gtccaccatt gaggaacagg ccaagacatt tttggacaag tttaaccacg aagccgaaga   180
cctgttctat caaagttcac ttgcttcttg gaattataac accaatatta ctgaagagaa   240
tgtccaaaac atgcgcccaa cccaagttca aggctgata agagagaaaa tctcatgatt   300
ttttcaa                                                              307

SEQ ID NO: 8              moltype = RNA  length = 307
FEATURE                   Location/Qualifiers
source                    1..307
                          mol_type = other RNA
                          organism = synthetic construct
SEQUENCE: 8
gggaaaaaag gaggttttag tctagggaaa gtcattcagt ggatgtgatc ttggctcaca    60
ggggacgatg tcaagctctt cctggctcct tctcagcctt gttgctgtaa ctgctgctca   120
gtccaccatt gaggaacagg ccaagacatt tttggacaag tttaaccacg aagccgaaga   180
cctgttctat caaagttcac ttgcttcttg gaattataac accaatatta ctgaagagaa   240
tgtccaaaac atgcgcccaa cccaagttca aggctgata agagagaaaa tctcatgatt   300
ttttccc                                                              307

SEQ ID NO: 9              moltype = DNA  length = 52
FEATURE                   Location/Qualifiers
source                    1..52
                          mol_type = other DNA
                          organism = synthetic construct
```

```
SEQUENCE: 9
taactttaag aaggagatat acatatgcat catcatcatc atcattcaca ag         52

SEQ ID NO: 10          moltype = DNA   length = 25
FEATURE                Location/Qualifiers
source                 1..25
                       mol_type = other DNA
                       organism = synthetic construct
SEQUENCE: 10
tgccggtttc agtggtgttg ccctg                                        25

SEQ ID NO: 11          moltype = DNA   length = 41
FEATURE                Location/Qualifiers
source                 1..41
                       mol_type = other DNA
                       organism = synthetic construct
SEQUENCE: 11
gcaacaccac tgaaaccggc atgctgcaac tgggtcagca c                      41

SEQ ID NO: 12          moltype = DNA   length = 50
FEATURE                Location/Qualifiers
source                 1..50
                       mol_type = other DNA
                       organism = synthetic construct
SEQUENCE: 12
tcagtggtgg tggtggtggt gctcgagtca ctctgccact ttttcttcg              50

SEQ ID NO: 13          moltype = DNA   length = 55
FEATURE                Location/Qualifiers
source                 1..55
                       mol_type = other DNA
                       organism = synthetic construct
SEQUENCE: 13
taatacgact cactataggg aaaaaggag gttttagtct agggaaagtc attca         55

SEQ ID NO: 14          moltype = DNA   length = 29
FEATURE                Location/Qualifiers
source                 1..29
                       mol_type = other DNA
                       organism = synthetic construct
SEQUENCE: 14
ttgaaaaaat catgagattt tctctctta                                    29

SEQ ID NO: 15          moltype = DNA   length = 29
FEATURE                Location/Qualifiers
source                 1..29
                       mol_type = other DNA
                       organism = synthetic construct
SEQUENCE: 15
gggaaaaaat catgagattt tctctctta                                    29
```